United States Patent [19]

Abernathy

[11] Patent Number: 4,936,302
[45] Date of Patent: Jun. 26, 1990

[54] SUPERFICIAL TEMPORAL ARTERY COMPRESSION CLAMP

[76] Inventor: Margaret Abernathy, 1815 Beulah Rd., Vienna, Va. 22180

[21] Appl. No.: 679,630

[22] Filed: Dec. 10, 1984

[51] Int. Cl.⁵ .............................................. A61B 17/00
[52] U.S. Cl. ................................ 606/158; 128/76 R; 433/73
[58] Field of Search ................. 128/346, 380, 76 R, 128/163, 75, 327, 1 R, 323; 433/73

[56] References Cited

U.S. PATENT DOCUMENTS

| | | | |
|---|---|---|---|
| 506,516 | 10/1893 | Lane | 128/380 |
| 737,473 | 8/1903 | Porter | 128/163 |
| 764,687 | 7/1904 | Shultz | 128/75 |
| 1,188,416 | 6/1916 | Dalbey | 433/73 |
| 1,557,988 | 10/1925 | Devine | 433/73 |
| 2,225,274 | 12/1940 | MacGoun | 128/76 R |
| 2,571,461 | 10/1951 | Livingston et al. | 128/327 |
| 3,463,157 | 8/1969 | Hunt | 128/76 R |
| 3,696,814 | 10/1972 | Umemoto | 128/380 |
| 3,884,240 | 5/1975 | Gilman | 128/346 |

FOREIGN PATENT DOCUMENTS 927243 5/1982 U.S.S.R. ............................ 128/1 R

Primary Examiner—Kenneth J. Dorner
Assistant Examiner—J. R. Hakomaki
Attorney, Agent, or Firm—James Creighton Wray

[57] ABSTRACT

A clamp to be used during the performance of cerebrovascular thermography wherein said clamp compresses superficial temporal arteries without introducing heat artifacts is disclosed. The clamp is provided with two oppositely disposed contact members, the distance between which is adjustable. Also, one contact member is provided with resiliency means.

28 Claims, 2 Drawing Sheets

SUPERFICIAL TEMPORAL ARTERY COMPRESSION CLAMP

BACKGROUND OF THE INVENTION

The invention pertains to geometrical instruments having opposed contact. These instruments may be applied to many fields, especially fields which use anatomical gauges and surgical hemostatic instruments which perform clamping and tourniqueting.

The present invention was designed to facilitate compression of superficial temporal arteries during performance of cerebrovascular thermography. Selective compression of various superficial facial vessels has always been an important part of non-invasive testing for internal carotid stenosis. Digital compression of the superficial temporal arteries, while adequate for periorbital Doppler evaluation, cannot be used in the thermographic examination because the heat of the technician's body would create artifacts on the thermogram. There are numerous structures for grasping and compressing in the various fields of art, yet nono so far has been able to surpass digital compression of the superficial temporal arteries in the performance of cerebrovascular thermography. This invention provides a solution to the problem of heat artifacts on the thermograms.

BRIEF SUMMARY OF THE INVENTION

The invention is a superficial temporal artery clamp to be used in the performance of cerebrovascular thermography. Superficial temporal arteries are palpated and marked and the superficial temporal artery clamp is then applied. The clamp comprises a grasping structure capable of accomodating various widths by the means of an adjustment mechanism. The contact members of this grasping structure comprise a resilient compressible material, the hardness of which is critical for compressing arteries located on either side of the human head. At least one of the contact members is assembled on a spring biased plunger assembly. This plunger assembly provides more resiliency to the contact member located thereon, thereby rendering the critical amount of pressure needed to compress the superficial temporal arteries more manageable.

The preferred embodiment is a V-shaped tong structure where two legs are hinged together. Bisecting both legs is the adjustment rod which slides through one leg and is threaded into the other leg. Upon turning the rod, an adjustment in width between the two legs is effected. The expanse of this rod stretching between the two legs is spring biased such that the two legs are maintained at the maximum width allowed by the rod. One may squeeze the tong diminishing the width between the two legs and increasing the spring tension. Releasing the tong, allows the spring to urge both legs apart to the extent allowed by the rod. The contact members are made of a rubberlike material the hardness of which is critical. One contact member is stationarily mounted on one leg of the tong. The other is oppositely disposed on a spring biased plunger assembly.

To fit the clamp, one depresses the plunger assembly, maximizing the width between the contact members and places the structure upon the patient's head. The stationary contact member is placed upon the correct spot and the plunger assembly with the other contact member is allowed to extend to another correct spot on another side of the patient's head. Further adjustments on the tension between the two contact members and the width between the two contact members is effected by the adjustment rod.

It is an object of this invention to provide an adjustable grasping structure with resilient contact members where the pressure applied in grasping is capable of minute management.

It is an object of this invention to provide an adjustable grasping structure with resilient contact members which is adapted to provide compression of the superficial peripheral arteries without creating artifacts on the thermogram.

It is another object of this invention to provide a relatively noninvasive compression of the superficial temporal arteries.

It is still another object of this invention to improve cerebrovascular thermography.

DETAILED DESCRIPTION OF THE INVENTION

Figure 1:
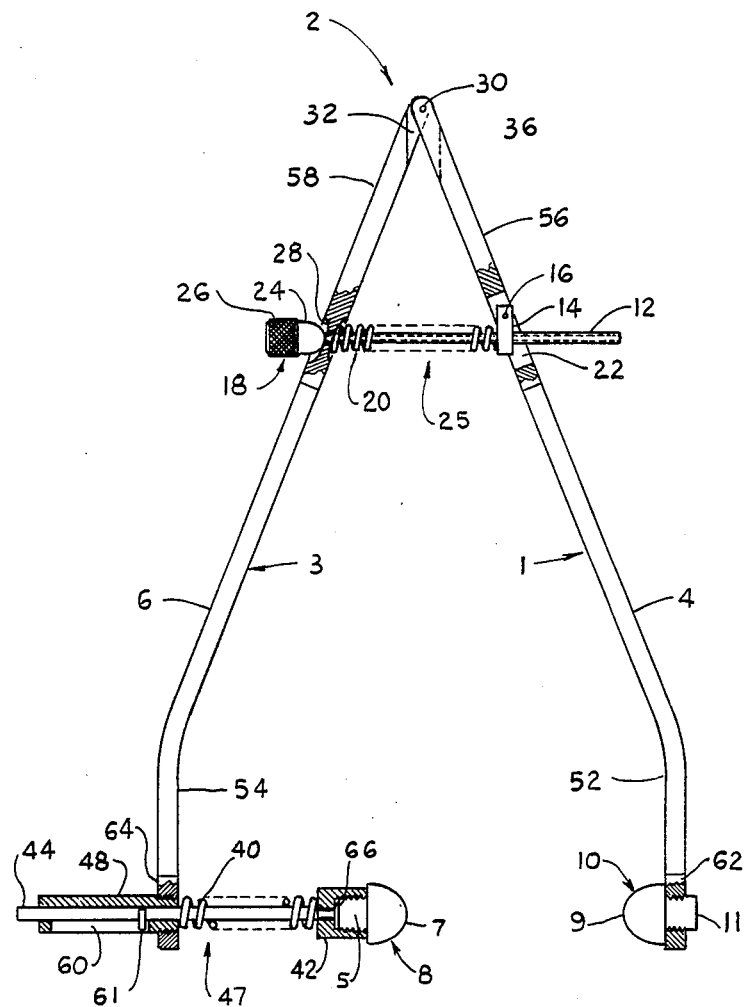
FIG. 1 is a frontal composite view of the superficial temporal artery clamp.

Thermography is a noninvasive test that depicts the body's invisible infrared energy in a visible format. The thermograph is an imaging radiometer which detects and collects infrared emanations from the skin and converts this energy into a "heat picture". Since the initial reports on the use of thermography in the diagnosis of cerebrovascular disease, significant refinements in thermographic instrumentation and technique have been made. At present, thermographic evaluation of the extracranial carotid complex is extremely sensitive in identifying individuals at risk for stroke.

Skin temperature is influenced primarily by subcutaneous blood flow. The temperature of the skin may also be affected by ambient temperature, humidity, air flow and radiant losses; however, blood flow in the carotid complex is the most important factor in the evaluation of a facial thermogram. Terminal branches of the ophthalmic artery leave the orbit and emerge on the forehead in the supraorbital region. Although most of the face is nourished by branches of the external carotid artery, the orbits and surrounding tissues receive blood primarily from terminal branches of the internal carotid artery. A normal facial thermogram shows temperature symmetry in areas nourished by these vessels. A color scale and a temperature reference source enable the physician to define actual temperatures.

Internal carotid stenosis with subsequent reduction in blood flow typically causes a significant ipsilateral decrease in periorbital tissue temperatures. Thermographically detects this temperature decrease and generates a picture of the abnormal heat patterns. After successful endarterectomy and resumption of blood flow through the internal carotid artery, the thermogram shows temperature symmetry in medial supraorbital regions.

Although transient monocular blindness frequently occurs in patients with internal carotid stenosis, relatively few individuals experience permanent loss of vision. Preservation of vision is usually ensured by multiple communications between branches of the internal and the external carotid arteries. As internal carotid stenosis develops, potential anastomotic channels may become functional and the ophthalmic artery may receive blood from one or more of these collateral channels, including the orbital branch of the middle meningeal artery. In such cases, the pictorial representation of elevated orbital temperatures on the thermogram may signal developing carotid stenosis long before clinical symptoms appear.

Another potential collateral source exists between the facial artery and the dorsal nasal branch of the ophthalmic artery. When flow relationships are normal between the internal and the external carotid arteries, the angular and lateral nasal branches of the facial artery remain small and typically the nose is cold. As internal carotid stenosis develops, there may be an increase in blood flow through the external carotid artery and its branches, including the facial artery and its terminal branches, the lateral nasal artery and the angular artery. The elevated nasal temperature resulting from this increased blood flow can be demonstrated on thermography.

Cerebrovascular thermography requires the use of relatively expensive equipment as well as a laboratory in which ambient temperature, humidity and air flow are meticulously controlled. The thermography technician must have a high level of skill and experience. In order to interpret the results, the physician needs an indepth knowledge of vascular anatomy and physiology, particularly of the multiple potential collateral channels that exist between terminal branches of the internal and the external carotid arteries. Thermography is emerging as a most sensitive indicator of developing stenosis in the carotid system and concomitant opening of collateral channels.

The superficial temporal artery clamp was designed to facilitate compression of the superficial temporal arteries during performance of cerebrovascular thermography. Selective compression of various superficial vessels has always been an important part of noninvasive testing for internal carotid artery stenosis. Digital compression of the superficial temporal arteries, while adequate for periorbital Doppler evaluation, can not be used in a thermographic examination because the heat of the technician's body would create artifacts on the thermogram. The superifical temporal artery clamp provides for superficial temporal compression without introducing heat artifacts.

Following performance of baseline cerebrovascular thermography, superficial temporal arteries are palpated and marked and the carotid artery clamp is applied. Thermograms are performed two minutes and five minutes following application of the clamp. In the last phase of the test, concomitant with the use of the superficial temporal artery clamp, the patient performs digital compression of the angular arteries bilaterally while additional thermograms are performed at two minutes and five minutes. No superficial temporal artery compression should be performed on any patient who has undergone external carotid/middle cerebral artery bypass. Such compression would compromise cerebrovascular profusion.

The invention can best be understood by referring first to FIG. 1. The clamp comprises two legs (1,3) connected together at their proximal ends with a hinge joint (2). It should be understood that any joint that permits motion in only one plane may be used. The hinge joint may best be seen in FIG. 2. As can be seen, the hinge joint consists of a central section (38) which is formed on the proximal end of leg (3). Leg (1) has its proximal end forked such that the sides of the fork form the ends of the hinge joint. Leg (1) and leg (3) are held together in the hinge arrangement with pen (30). Space (34) located on the proximal end of leg (1) provides room for proximal end of leg (3) denoted as (32) in FIG. 1 to swing both towards leg (1) and away from leg (1). The proximal end of leg (3) is diminished in width such that it forms a central part of the hinge joint and is wide enough to fit between the two sides of the fork as denoted in FIG. 2 on the proximal end of leg (1).

Located distally from the hinge joint is the adjustment means (25). The adjustment means comprises a rod (12), a nut with internal threads (14), a hinge pin (16) which holds nut (14) in perpendicular alignment to rod (12) in open space (22) on leg (1), headed in (18) on rod (12) which is attached to rod (12) by way of a longitudinal bore in head (18) by means of a set screw (26), and a spring (20) wrapped helically around a section of rod (12) spanning the distance between leg (3) and leg (1).

As can be seen, leg (3) has a hole for slideably engaging rod (12) wherein this hole is recessed somewhat into leg (3) as denoted by (28). The head (18) prevents the rod from extending completely through the hole on leg (3). The head also contains a friction surface denoted by the crosshatchings to facilitate grasping and turning of this rod. The rod is inserted into the hole on leg (3) to the point of having the headed end abutt the outer surface, then threadably engages the nut located on leg (1). A spring located on the expanse of rod (12) extending between the two legs at once urges both legs away from each other. A turning of the head (18) causes the rod (12) to threadably engage nut (14) and either closes the distance between leg (1) and (3) or widens the distance between leg (1) and (3). The spring at all times keeps the legs expanded the maximum distance allowed by the rod (12).

Each leg (1) and (3) is bent inwardly at points (54) and (52) such that the distal ends of said legs are brought into substantial parallel alignment. Leg (1) has attached to its distal end a contact member (10). The contact member is rounded denoted by the numeral (9) and is constructed of a compressible material. Preferably the material used is room temperature vulcanizing rubber (RTV rubber). Dow Corning makes the material under the tradename "SILASTIC-E". The hardness of this rubber is denoted 35–40A. This means 35–40 on the A scale. It is understood that any prevalent rubber or resilient means may be used and several are made by various companies. The contact member (10) is attached to leg (1) by threadably engaging a hole with internal threads located distally on leg (1). The contact member is a hemispherical structure with a longitudinal cylindrical extension projecting from the flat side of the hemisphere. This longitudinal cylinder denoted as (11) threadably engages hole (62) on the distal end of leg (1).

Leg (3) is provided with a plunger apparatus (47) located distally on leg (3). This apparatus comprises a reciprocating rod (44), a cylinder (48) with a longitudinal bore for receiving the reciprocating rod (44), a longitudinal groove (60) which extends along cylinder (48) and provides an opening between the outside and the longitudinal bore, stop pin (61) which extends radially from reciprocating rod (44) and into groove (60), spring (40) helically wrapped around the section of reciprocating rod (44) extending from the innerface of leg (3) to the cylinder head (42), cylinder head (42), and contact member (8).

The distal portion of leg (3) comprises the resiliency means of the carotid artery clamp. Essentially when one puts pressure on surface (7) of contact member (8), the rod (44) is pushed back into cylinder (48), but only so far as stop pin (61) is allowed to travel in groove (60). When no pressure is on surface (7), spring (40) urges the cylinder head with the contact member attached thereto away from the distal end of leg (3) and towards the oppositely disposed contact member (10) distally located on leg (1). The stop pin (61) prevents the spring (40) from urging reciprocating rod (44) completely out of cylinder (48).

Figure 3:
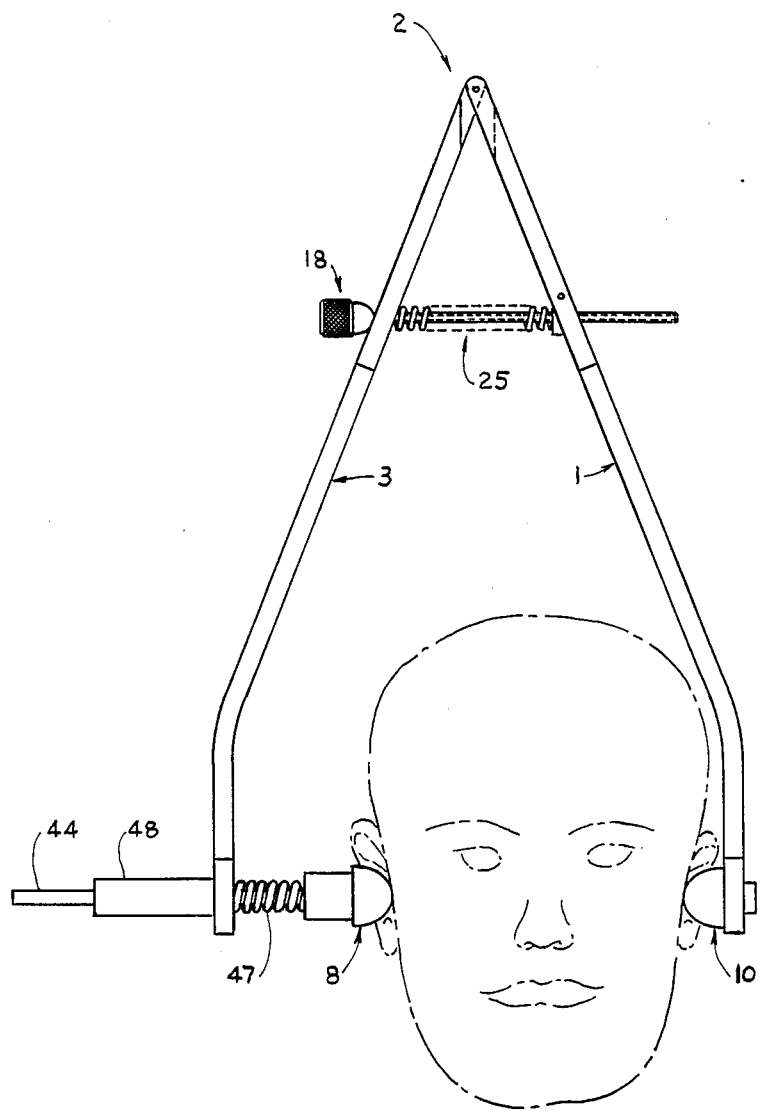
FIG. 3 is a plan view of the superficial temporal artery clamp as it would be positioned on a patient.

The mode of use contemplated by the inventor is best depicted in FIG. 3. The superficial temporal artery clamp is placed around the head of the patient such that contact members (10) and (8) palpate and compress temporal arteries. Should the legs of the clamp (1) and (3) need to be widened to accommodate various sized heads, adjustment means (25) may be adjusted by turning adjustment rod head (18) to bring the distal ends of legs (1) and (3) closer or farther apart. Simply put, contact members (8) and (10) are manually spread apart and fit over the arteries to be compressed and the tightness of the contact members is adjusted by means of adjustment means (25).

Figure 2:
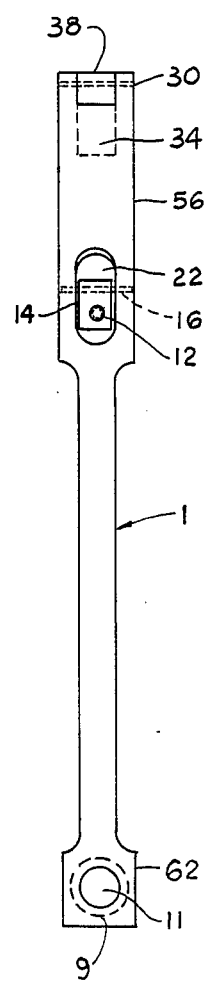
FIG. 2 is a side view of the artery clamp depicting the outer surface of the leg generally indicated as numeral 1.

Referring to FIG. 2, the nut threadably engaging adjustment rod (12) is capable of maintaining perpendicular alignment with said rod by virtue of being able to pivot upon pin (16) within hole (22) on leg (1).

The construction of this apparatus is simple. The legs (1) and (3) are similar in shape. It is preferable to start with elongated flat pieces which are of a light alloy. Referring to FIG. 2, each piece is to be machined so that there is a portion of each leg indented from both sides (See FIG. 2). Each piece is to be bent at a point a short way proximally located from the distal end. Preferably the bend describes an obtuse angle approximately 150 degrees 30 seconds. The distal ends are spatulate in shape due to the aforementioned machining and a hole is machined in the spatulate areas extending from the outer surface to the inner surfaces of the pieces wherein the holes are provided with internal threads. The proximal ends are rounded off and a hinge bore is drilled through each rounded end wherein said bore is perpendicular to the holes in the spatulate distal ends.

At this point, the two legs are differentiated.

Leg (3) has the proximal end machined at area (32), FIG. 1, and this provides a central portion of the hinge joint. Leg (1) has a portion cut out of the center of the proximal end which corresponds to the width of the indented proximal end of leg (3). Leg (3)'s proximal end is fit into the central cavity of leg (1)'s proximal end and the hinge bores are lines up and the hinge pin is inserted. The indented proximal end (32) on leg (3) and the central bite cut out of the proximal end of leg (1) are angular so as to limit the extension and flexion of the hinge joint.

Construction of the adjustment means (25) is likewise simple. At a point somewhat distally located from the proximal hinge joint on leg (3), a hole is drilled from the outer surface to the inner surface wherein said hole slideably receives a rod (12). The outer and inner surfaces of the hole may be recessed as shown in (28) FIG. 1. Leg (1) has a somewhat differently shaped hole cut at approximately the same point corresponding to the hole on leg (32) wherein said hole corresponds to numeral (22) shown in FIG. 2. Referring to FIG. 2, the hole is approximately oblong in shape where a rectangular nut is located. This nut is held in place by a pivot pin (16). The hole holding pivot pin (16) is drilled in much the same fashion and in the same direction as the hinge bore holding the hinge pin (30). This pivot pin (16) allows the nut to maintain perpendicular alignment to rod (12) which threadably engages the internal threads in nut (14). The adjustment rod may be any rod which has one end with threads to engage nut (14) and the other end capable of being inserted into a enlarged head (18). Head (18) may be of any suitable material and may contain a longitudinal bore wherein the smooth end of rod (12) may extend into the longitudinal bore of head (18) and a set screw may affix head (18) onto rod (12). Rod (12) then is inserted threaded end first into the hole at (28) FIG. 1 and extended all the way through the hole until head (18) abutts with hole (28) and the threaded end of rod (12) is threaded through nut (14). A spring is helically wrapped around the section of rod (12) which extends across the space between legs (3) and (1). The spring keeps the legs (1) and (3) extended to the maximum extent allowed by rod (12).

The distal end of leg (3) is provided with resiliency means denoted by the numeral (47). The construction of the resiliency means is likewise simple. A longitudinal cylinder (48) provided with a longitudinal bore extending therethrough, is threadably attached to the hole located in the spatulate distal end (64). This cylinder has a groove (60) located along the side of the cylinder. The groove extends all the way from the outside to the longitudinal bore. The reciprocating rod (44) which extends through the longitudinal bore of cylinder (48) has a stop pin (61) radially extending from the rod and into the groove (60). Groove (60) forms a channel permitting the movement of stop pin (61) within the channel. The reciprocating rod (44) is merely a smooth rod which may be inserted into the longitudinal bore. Once inserted into the cylinder the stop pin may be attached to the reciprocating rod through the channel or groove (60). The stop pin may be in the form of a set screw or any axial extension which may be attached to the reciprocating rod and extend into the channel from the longitudinal bore. Once the reciprocating rod is inserted into the bore, the stop pin is inserted through the channel and onto the reciprocating rod. The rod is held in place within the cylinder and may only reciprocate as much as the stop pin may move in the channel (60). A spring (40) is then helically wrapped around the section of rod (44) extending from the inner surface of leg (3). A cylindrical head (42) is then inserted over the end of reciprocating rod (44) to provide a head for said rod. This cylindrical head (42) provides an end for spring (40) to be maintained between the inner surface of the distal end of leg (3) and the cylindrical head (42). Cylindrical head (42) may be fit upon reciprocating rod (44) by threadably engaging threads located on the end of reciprocating rod (44).

Cylindrical head (42) has a hole partially machined therethrough with internal threads (66) to threadably engage contact member (8). Contact member (8) has a hemispherical surface (7) with a longitudinally extending piece (5) to threadably engage cylindrical head (42). Contact member (9) similar in structure to contact member (8) also has a hemispherical surface (10) with a longitudinal piece (11) threadably engaging hole (62).

The aforementioned details of the construction of the preferred embodiment is not to be construed as limiting the scope of the invention in any way. The hinge joint (2) may be any kind of attachment which permits the extension and flexion of two grasping members. Legs (3) and (1) may be constructed of any suitable material including lightweight alloys or polyvinylchloride plastic. The adjustment means (25) on FIG. 1 may be any spring biased screw adjustment. The resiliency means (47) may be any spring biased plunger assembly. Any of these pieces may be constructed out of machined metal or plastic. The contact members (7) and (9) are preferably constructed of rubber having the hardness 35–40A. This means 35–40 on the A scale. Dow Corning makes a suitable product called "SILASTIC-E". The product code is EF062842. It is understood that any room temperature vulcanized rubber may be substituted so long as the degree of hardness is maintained. The degree of hardness is very critical in compressing the temporal arteries.

Having described my invention with particularity and disclosing how it is made and used, I now set out the scope of my invention embodied within the claims.

What I claim is:

1. A superficial temporal artery clamp comprising:
   (a) means for grasping having first and second oppositely disposed pieces;
   (b) resiliency means distally located on said second piece;
   (c) a first contact member distally located on said first piece;
   (d) a second contact member mounted on said resiliency means, wherein said second contact member is oppositely disposed said first contact member, whereby variations in distance between said contact members is subject to expansion when said second contact member is confronted with sufficient pressure to cause said resiliency means to retract such that said second member is urged away from said first contact member;
   (e) means for adjusting said means for grasping mounted integrally therein, whereby variations in distance between said first and second oppositely disposed pieces are effected.

2. The device of claim 1 where said first and second oppositely disposed pieces further comprises having first and second ends, wherein said first ends are connected by means for hinging.

3. The device of claim 1 where said resilient means further comprises a spring mounted between said second contact member and said second oppositely disposed piece.

4. The device of claim 3 where said spring further comprises being helically wrapped around a reciprocating rod.

5. The device of claim 4 where said resilient means further comprises a hollow cylinder adapted to slideably receive said reciprocating rod.

6. The device of claim 5 where said cylinder further comprises means for maintaining said reciprocating rod in sliding relationship with said cylinder.

7. The device of claim 1 where said contact members are made from room temperature vulcanizing rubber.

8. The device of claim 1 where said contact members are made of "SILASTIC-E".

9. The device of claim 1 where said means for adjusting further comprises a headed screw.

10. The device of claim 9 where said means for adjusting further comprises a hole for slideably receiving said headed screw located on said first oppositely disposed piece and a corresponding hole adapted to threadably engage said headed screw located on a corresponding point on said second oppositely disposed piece.

11. The device of claim 10 where said means for adjusting further comprises said heated screw extending through said hole on said first oppositely disposed piece and threadably engaging said hole on said second oppositely disposed piece.

12. The device of claim 11 where said means for adjusting further comprises a spring helically wound around said screw located between said first and second oppositely disposed pieces, whereby said spring urges both oppositely disposed pieces away from each other.

13. A superficial temporal artery clamp, comprising:
   (a) first and second legs having proximal and distal ends, said legs being connected together at said proximal ends by means for connecting, whereby said means for connecting maintain said legs in an acute angle with respect to each other, whereby a tong is formed having two legs and said legs have inner and outer surfaces;
   (b) means for adjusting said acute angle located distally on said tongs from said means for connecting;
   (c) a first resilient pad attached to said inner surface of said distal end of said first leg;
   (d) means for receiving a plunger provided on said distal end of said second leg;
   (e) a plunger slideably received in said means for receiving;
   (f) a second resilient pad attached to said plunger, said second pad facing and being oppositely disposed to said first pad, and wherein said second pad is urged toward said first pad by said means for urging, whereby an object may be held securely between said pads with adjustments on the pressure on such pads being made when necessary by manipulating said means for adjusting.

14. The device of claim 13 where said means for connecting further comprises a hinge joint.

15. The device of claim 1 where said legs are bent inwardly at said distal ends such that said distal ends are brought into approximate parallel alignment.

16. The device of claim 1 where said means for adjusting further comprises a rod having first and second ends wherein said first end is provided with a head and said second end is provided with threads.

17. The device of claim 16 where said means for adjusting further comprises a first hole located on said first leg which is adapted to slideably receive said rod.

18. The device of claim 17 where said means for adjusting further comprises a hole located on said second leg for threadably engaging said rod.

19. The device of claim 18 where said means for adjusting further comprises said rod slideably extending through said first hole in said first leg and threadably engaging said second hole in said second leg.

20. The device of claim 19 where said means for adjusting further comprises a spring helically wrapped around said rod between said first and second holes.

21. The device of claim 1 where said first and second resilient pads are made of room temperature vulcanizing rubber.

22. The device of claim 1 where said first and second resilient pads are made of "SILASTIC-E".

23. The device of claim 1 where said means for receiving a plunger further comprises a cylinder having a longitudinal bore adapted to slideably receive said plunger.

24. The device of claim 23 where said plunger further comprises a smooth rod with first and second ends, wherein said first end is attached to said second resilient pad and said second end is adapted to slideably communicate with said longitudinal bore.

25. The device of claim 24 where said plunger further comprises a spring helically wrapped around said rod and located between said second resilient pad and said interface of said second leg.

26. The device of claim 1 where said means for urging is a spring.

27. A superficial temporal artery clamp, comprising:
(a) first and second legs each having proximal and distal ends and each having an outer and inner face, said legs being connected at said proximal ends by a hinge joint, whereby a V-shaped tong is formed having inner and outer surfaces, wherein said distal ends are bent inwardly such that said ends are substantially parallel in relationship;
(b) a hole located distally from said hinge joint on said second leg and extending therethrough, said hole having an outer opening on said outer face and an inner opening on said inner face, said hole adapted to slideably receive an adjustment rod;
(c) a hole located distally from said hinge joint on said first leg and extending therethrough, said hole having an outer opening on said outer face and an inner opening on said inner face, said hole provided with a perforated metal block, immovably placed therein, having internal screw threads adapted to engage a screw for tightening, whereby said metal block is a nut;
(d) an adjustment rod having a threaded end and a headed end extending, threaded end first, into said outer opening on said second leg, said headed end abutting said outer opening, said headed end being larger than said outer opening, said threaded end threadably engaging said nut on said first leg, whereby said adjustment rod maintains said first and second legs of said tong in relationship to each other such that a turning of said headed end in one direction urges said legs in closer proximity and a turning of said rod in another direction allows for said legs to move farther away from each other;
(e) a first spring helically wound around said adjustment rod and located between said first and second legs;
(f) a resilient pad attached to said inner face of said distal end of said first leg;
(g) a hole with an outer face opening and an inner face opening located on said distal end of said second leg and extending transversely therethrough and adapted to slideably receive a smooth rod;
(h) a cylinder with first and second ends having a longitudinal bore extending therethrough attached to said outer face of said distal end of said second leg by means for attaching, said longitudinaal bore in alignment with and communicating with said hole in said distal end of said second leg, wherein said cylinder is further provided with an elongated longitudinally extending channel, having proximal and distal ends, said channel being parallel to said longitudinal bore, said channel provided with an opening on an outside surface of said cylinder, and an opening on an inside surface of said cylinder, whereby said channel spans a substantial length of said cylinder and provides a space extending from said outer surface of said cylinder to said longitudinal bore;
(i) a smooth rod with first and second ends, said second end slideably extending through said inner face opening of said hole on said distal end of said second leg and extending through said longitudinal bore of said cylinder, whereby a telescoping relationship is defined, said rod being further provided with a radially extending stop pin wherein said stop pin extends radially from said rod and into said channel, whereby said telescoping relationship is at once maintained by said stop pin and limited by said stop pin;
(j) a cylinder with first and second ends wherein said first end is fixed to said first end of said smooth rod by means for attaching, whereby said cylinder is larger than said inner face opening of said hole on said distal end of said second leg, whereby a cylinder head is defined;
(k) a second spring helically wound around said smooth rod located between said cylinder head and said inner face of said second leg;
(l) a second resilient pad affixed to said second end of said cylinder head by means for attaching, said second pad facing and oppositely disposed to said first pad.

28. The method of compressing superficial temporal arteries in the performance of cerebrovascular thermography, comprising the steps of:
(a) placing a superficial temporal artery clamp upon a patient's head; and
(b) adjusting the tension of said clamp; and
(c) compressing the designated arteries to the extent necessary to decrease resistance in the superficial temporal artery
wherein said clamp comprises a device for grasping having first and second oppositely disposed pieces, resiliency means distally located on said second piece, a first contact member distally located on said first piece, a second contact member mounted on said resiliency means, wherein said second contact member is oppositely disposed to said first contact member, whereby variations in distance between said contact member, whereby variations in distance between said contact members is subject to expansion when said second contact member is confronted with sufficient pressure to cause said resilience means to retract such that said second member is urged away from said first contat member, and means for adjusting said means for grasping mounted integrally thereon, whereby variations in distance between said first and second oppositely disposed pieces are effected.

* * * * *